United States Patent
Vilsmeier et al.

(10) Patent No.: US 6,783,536 B2
(45) Date of Patent: Aug. 31, 2004

(54) MAGNETIC CATHETER NAVIGATION

(75) Inventors: Stefan Vilsmeier, Kufstein (AT); Jens Witte, München (DE); Rainer Birkenbach, Poing (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 28 days.

(21) Appl. No.: 10/134,979

(22) Filed: Apr. 29, 2002

(65) Prior Publication Data

US 2003/0114778 A1 Jun. 19, 2003

(30) Foreign Application Priority Data

Dec. 14, 2001 (EP) .............................. 01129329

(51) Int. Cl.⁷ .............................. A61B 19/00
(52) U.S. Cl. ...................... 606/130; 600/424
(58) Field of Search ................... 128/899; 600/117, 600/145, 424, 585; 606/130, 129

(56) References Cited

U.S. PATENT DOCUMENTS 4,950,232 A    8/1990 Ruzicka et al.
6,474,341 B1 * 11/2002 Hunter et al. ............... 128/899

FOREIGN PATENT DOCUMENTS

| DE | 100 22 937 | 11/2001 |
| EP | 0 425 319 | 5/1991 |
| WO | 96/05768 | 2/1996 |
| WO | 97/29710 | 8/1997 |
| WO | 01/67035 | 9/2001 |

* cited by examiner

*Primary Examiner*—David O. Reip
(74) *Attorney, Agent, or Firm*—Renner, Otto, Boisselle & Sklar, LLP

(57) ABSTRACT

The invention relates to a device for maneuvering a catheter into the interior of a body, comprising a support stiletto (5) which may be inserted into the catheter tube (1) and which sustains the shape of said catheter tube (1) as it penetrates into the interior of the body, wherein a position-indicating magnetic tracking portion (7, 8, 9, 10) is arranged on said support stiletto (5) which may be detected by means of a magnetic tracking-based navigation portion (11, 12).

14 Claims, 1 Drawing Sheet

MAGNETIC CATHETER NAVIGATION

Figure 1:
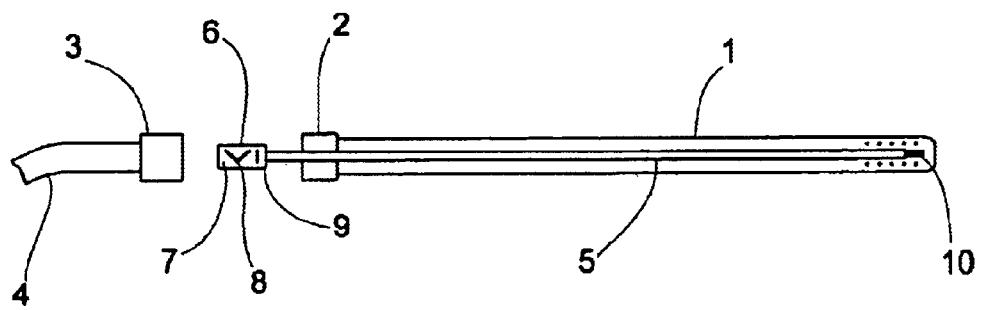

The present invention relates in general to magnetic catheter navigation and in particular to a device for maneuvering a catheter into the interior of a body, comprising a support stiletto which may be inserted into the catheter tube and which sustains the shape of the catheter tube as it penetrates into the interior of the body.

Such catheters and/or devices are used for example when liquid is to be drained from the interior of the body. When for example after a head injury, an oedema forms in the interior of the patient's brain, i.e. an area in which liquid accumulates, this must be drained as quickly as possible in order to avoid significant brain damage due to the high intercerebral pressure. To this end, catheters are currently used in accident medicine which are inserted by hand through a bone opening to be produced into the brain of the patient, such that the tip of the catheter comes to rest in the zone where the accumulation of liquid is forming. The catheter tube is provided with perforations at its tip, through which the liquid can pass into the interior of the tube, to then be transported away. Another area of application is the case of inborn hydrocephalus, in which overproduction of cerebral liquor leads to an excessive interior cerebral pressure, such that this liquor constantly has to be drained, in the course of which the catheter is placed under the skin, from the brain to the abdominal region.

For inserting the tip of the catheter into the correct position, experienced staff currently use another method in which the correct angle of penetration and the correct point of penetration are identified manually, for example by way of the bone seams of the cranium. This method, however, can be inaccurate even when performed by experienced medical staff, and inexperienced physicians have even greater difficulties in exactly positioning the tip of the catheter. Precisely in the brain area, however, every deviation is critical, since the consequences of an insertion error, namely damage to healthy tissue and an insufficient amount of liquid being transported away, can be fatal.

It is therefore the object of the present invention to provide a device for maneuvering a catheter into the interior of a body, which ensures that the tip of the catheter is accurately placed and reliably inserted correctly by the medical staff. In particular, it is intended that such a treatment be possible in an environment in which only a low level of apparatus is available.

This object is solved in accordance with the invention by the subject of patent claim 1. The sub-claims define preferred embodiments of the present invention.

In accordance with the invention, a position-indicating magnetic tracking means is arranged on the support stiletto for the catheter tube, said device being detectable by means of a magnetic tracking-based navigation means. In other words, the stabilization means which is necessary anyway for inserting the catheter tube is simultaneously used as a positioning aid which can be used in an environment in which a magnetic tracking-based navigation means is available. Such magnetic tracking-based navigation means do not require a costly camera system, such as for example optically based navigation means, and are therefore ideally suited to catheter navigation in the sense in accordance with the invention. Computer tomography data or nuclear spin tomography data are used for registering and currently detecting the body part co-ordinates. To this end, a CT or MR image is taken of the patient before he is treated.

The physician introducing the catheter can then check on the screen of the magnetic tracking navigation system whether the target point has been hit or whether corrections still need to be made. Moreover, the navigation system can even make suggestions as to the length of penetration, the point of introduction or the angle of introduction, and/or can indicate an incorrect insertion through warning indicators. In this way, two- and three-dimensional representations are available to the staff on the screen of the navigation system.

The catheter is inserted into the interior of the body using the stiletto, necessary for stabilization and introduced into the catheter tube, and precisely this stiletto can support the magnetic tracking means in accordance with the invention. Once the catheter has been positioned, the stiletto can be withdrawn from the rear end, where a drainage hose can then be attached to the catheter tube via an adaptor.

Said magnetic tracking means can comprise miniature coils, at least two coils being advantageously provided which are spatially orientated differently. Using such an arrangement of coils, a positional tracking of the catheter can be realised which may be determined in all degrees of freedom. It should also be noted here that it is fundamentally important in the present invention to establish or navigate the angle of penetration and depth of penetration such that it can in principle be sufficient to provide a single miniature coil on the stiletto, since navigation is relatively non-critical with respect for example to the rotation of the stiletto and/or the catheter tube about the longitudinal axis.

In one embodiment of the present invention, a first coil is arranged on the area of the stiletto facing away from the tip, while a second coil is arranged on the tip of the stiletto. Specifically arranging one coil on the tip of the stiletto enables the depth of penetration and direction of penetration to be very accurately detected, when the other coil is positioned relatively far away at the end of the stiletto facing away from the tip.

In accordance with another embodiment of the invention, a pair of coils consisting of coils which are spatially orientated differently is arranged at the end of the stiletto facing away from the tip, in particular in or on a grip means of the stiletto, where sufficient space is available even for arranging larger coils.

Any combination of the number of coils and the positioning of the coils can of course be selected, as long as the navigational tasks can be fulfilled.

In an embodiment of the invention, the stiletto is connected to the navigation means, for transferring signals or energy via a cable. In this way, for example, induction currents can be transmitted to the coils or induced currents read from the individual coils.

In accordance with another embodiment, the stiletto comprises a means for wireless signal exchange with the navigation means, and in particular an energy supply of its own. In this way, a "cable-free" stiletto can be realised which allows the treatment staff an extensive freedom for treatment and great freedom of movement.

The stiletto is advantageously designed as a disposable item together with the magnetic tracking means, and in particular is provided sterilely packed, together with or separate from the catheter tube.

In a particularly preferred embodiment, the catheter is a head and/or brain catheter.

In order to be able during navigation to also take into account movement of the part of the body into which the catheter is to be inserted, a reference sensor is attached in a fixed positional assignment to said part of the body. Advantageously, this reference sensor is again an arrangement of coils which can be spatially tracked and communicates its movement data to the navigation system via a cable or by radio.

There are a number of options, according to the part of the patient's body in question, for fixing such a reference sensor. A headset could for example be used, such as is known from navigation for ear, nose and throat treatments, an elastic band (headband) or an adhesive tape with a reference sensor can be used. A preferred embodiment of the present invention uses an affixed reference sensor, in particular when the catheter to be positioned is a head or brain catheter. In such a case, it is advantageous to fix the reference sensor to a tooth on the upper jaw. In this way, the reference sensor can on the one hand be affixed directly to the patient's tooth, for example using a tooth adhesive such as is used for fixing braces. In a particularly preferred embodiment, the reference sensor is fixed to an upper jaw tooth via an intermediate adaptor, i.e. only the adaptor is firmly affixed, and the reference sensor can be attached to the adaptor, for example plugged into it.

A patient with such a reference sensor on a tooth can easily close his mouth during magnetic navigation. General advantages are simple handling, very high accuracy and the fact that it is not possible for the sensor to slip during treatment. The embodiment comprising the intermediate adaptor affixed to the tooth also has the advantage that the sensor does not have to be attached until just before treatment, and can be repeatedly reused.

Figure 2:
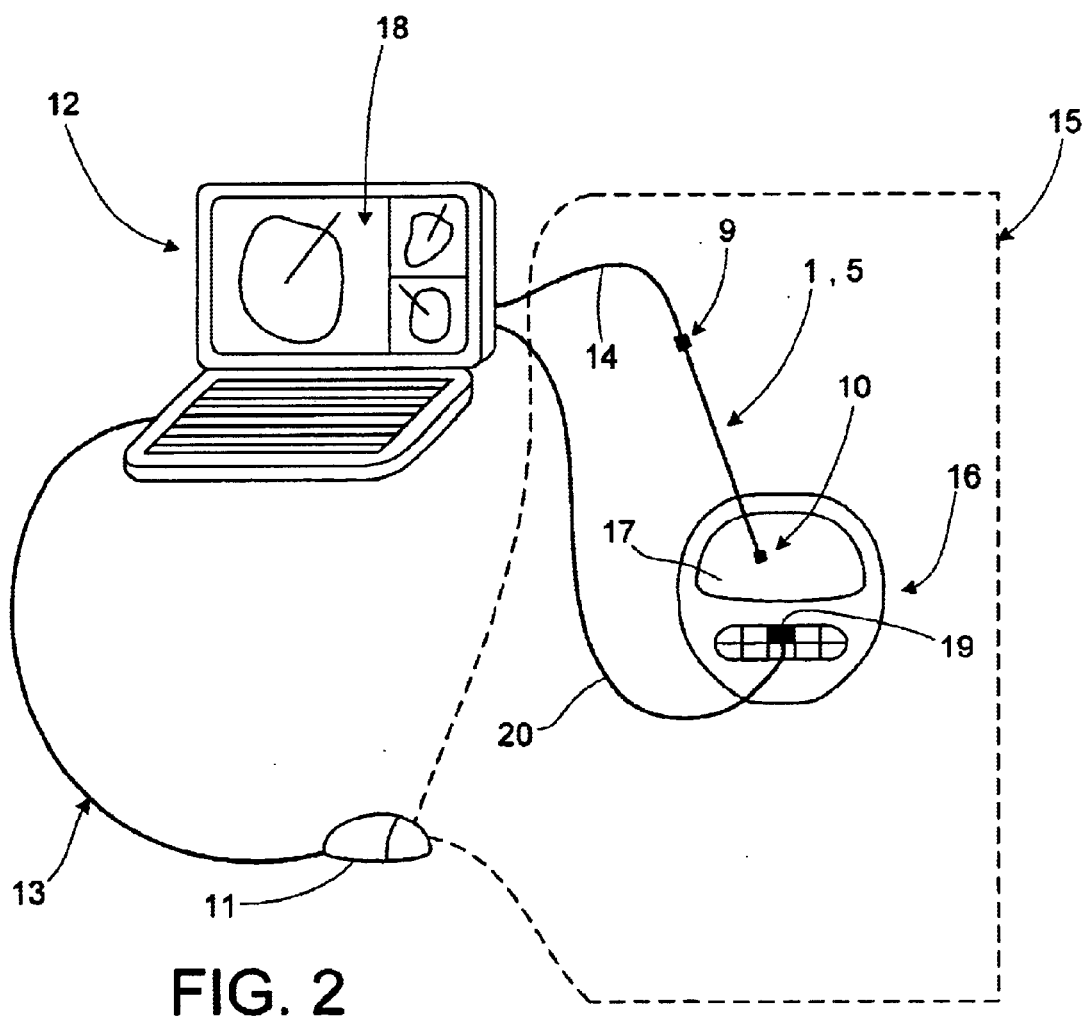

The invention will now be described by way of an embodiment. Reference is made in this respect to the accompanying drawings; there is shown:

FIG. 1 a schematic representation of a device in accordance with the invention, comprising a catheter and an introduced stiletto which may be navigated using magnetic tracking; and FIG. 2 a schematic representation for the technical environment within the context of magnetic catheter navigation in accordance with the invention.

FIG. 1 schematically shows the device in accordance with the invention. It comprises a catheter tube 1 which comprises a connecting adaptor at the end shown on the left and exhibits perforations (not shown) at its end shown on the right, the tip. Through these perforations, liquid can pass into the interior of the catheter tube. The catheter tube is designed to be very thin and consists of a soft plastic material. A catheter hose 4 is also shown on the left in FIG. 1, which via its adaptor 3 can be connected to the connecting adaptor 2 of the catheter tube 1 when the stiletto 5 is withdrawn again, after having been inserted into the catheter.

The stiletto 5 just mentioned is inserted into the catheter tube 1 in order to support it when the catheter tube is inserted into the interior of the body. It substantially reaches up to the tip of the catheter tube 1 and can comprise a kind of grip piece 6 at its end facing away from the tip, said gripping piece 6 being fixed to a part of the stiletto 5 projecting behind over the connecting adaptor 2. The stiletto 5 is made of a very thin but strong material.

Furthermore, possible arrangements of miniature coils are shown in FIG. 1 which are attached to the stiletto for magnetic navigation. On the one hand, a pair of coils 7, 8 can be situated in the grip piece, wherein the coil 7 and the coil 8 are respectively arranged in different spatial directions, in the present example they are V-shaped with respect to each other. The pair of coils 9, 10 are also shown as an option, wherein the coil 10 is arranged in the axial direction on the tip (right) of the stiletto 5, while the coil 9 is perpendicular to the axial direction in the grip piece 6. With the aid of such arrangements of coils, the stiletto 5 can be three-dimensionally navigated and three-dimensionally tracked in a known way, and thus the surrounding catheter tube 1 as well, until the tip of the catheter tube is sat at the correct point in the interior of the body. The stiletto 5 is then withdrawn from the catheter tube 1 at the grip piece 6, and the catheter tube 1 and the hose 4 can be connected with the aid of the adaptors 2 and 3; the excess liquid can then drain off.

FIG. 2 schematically shows the technical environment for a method comprising the device in accordance with the invention. A navigation system is provided comprising the computer and display unit 12 which comprises a screen 18 and input elements (not shown) as well as plug connections for other components. A field generator 11 is connected to one such plug connection by means of a cable 13, said field generator 11 establishing a magnetic tracking field whose outline is indicated by a broken line and provided with the reference numeral 15. The schematically shown head 16 of a patient is situated within this field 15, an accumulation of liquid having formed in the likewise schematically shown brain structure of said head 16.

The system further comprises a so-called reference sensor 19 which follows the movement of the part of the patient's body and is therefore fixedly arranged on said body part. In the present case, the reference sensor 19, which is to be connected immovably to the patient's head 16, is attached to a tooth of the patient's upper jaw. It likewise consists of an arrangement of coils which allows spatial positional detection in the magnetic tracking system. The sensor 19 is likewise connected to the computer and display unit by means of a cable, such that the movements of the head 16 in the navigation system made while the catheter is being positioned are known and can be calculated into navigation. In magnetic navigation, it is not a problem if the patient closes his mouth over the reference sensor 19. In the present case, the reference sensor 19 is attached via an adaptor affixed to the tooth, such that it only has to be placed there before treatment and can be repeatedly reused. It is of course also possible to affix the reference sensor 19 directly to a tooth in the area of the patient's upper jaw; in both cases, the sensor is excluded from slipping during treatment.

In the embodiment shown, a catheter hose provided with a stiletto has been inserted into the brain using a cable 14. The two components are indicated by 1, 5. At the end of the tip and at the end of the stiletto facing away from the tip, respectively, a coil 10 and/or 9 is indicated in a disproportionately large representation, which are arranged like the corresponding components in FIG. 1. In the state shown, the physician who is to position the catheter can check on the display device 18 how far and at what angle the catheter has already been inserted, and make corresponding corrections or guide the correct insertion of the catheter. The navigation system receives the information about this from the positions of the coils 9 and 10 in the field 15 generated by the generator 11. Once the catheter has been corrected inserted, the stiletto 5 is then removed as described above and the liquid can begin to be drained.

Through the present invention, therefore, even inexperienced treatment staff have the option of positioning such a catheter accurately and without unnecessarily injuring healthy tissue, while experienced physicians are always able to check whether the catheter has been positioned successfully.

What is claimed is:

1. A device for maneuvering a catheter into the interior of a body, comprising a support stiletto that may be inserted into a catheter tube and that sustains the shape of said catheter tube as it penetrates into the interior of the body, and a position-indicating magnetic tracking means arranged on said support stiletto which may be detected by means of a magnetic tracking-based navigation means, wherein said magnetic tracking means comprises at least two miniature coils that are spatially orientated differently.

2. The device as set forth in claim 1, wherein a first coil is arranged on the area of said stiletto facing away from the tip, while a second coil is arranged on the tip of said stiletto.

3. The device as set forth in claim 1, wherein a pair of coils that are spatially orientated differently are arranged at the end of said stiletto away from the tip.

4. The device as set forth in claim 3, wherein said pair of coils are arranged in or on a grip of said stiletto.

5. The device as set forth in claim 1, wherein said stiletto is connected to said navigation means for transferring signals or energy by means of a cable.

6. The device as set forth in claim 1, further comprising the navigation means, and wherein said stiletto comprises a means for wireless signal exchange with said navigation means.

7. The device as set forth in claim 6, wherein said stiletto further comprises an energy supply of its own.

8. The device as set forth in claim 1, wherein said stiletto is designed as a disposable item together with the magnetic tracking means.

9. The device as set forth in claim 8, wherein said stiletto and said magnetic tracking means are sterilely packed together with or separate from said catheter tube.

10. The device as set forth in claim 1, wherein said catheter is a head or brain catheter.

11. A device for maneuvering a catheter into the interior of a body, comprising
   a support stiletto that may be inserted into a catheter tube and that sustains the shape of said catheter tube as it penetrates into the interior of the body,
   a magnetic, tracking-based navigation means,
   a position-indicating magnetic tracking means arranged on said support stiletto that may be detected by means of said magnetic, tracking-based navigation means, and
   a reference sensor that is fixedly attached to the part of the body into which the catheter is inserted and that is detectable by said navigation means.

12. The device as set forth in claim 11, wherein said catheter is a head or brain catheter, and said reference sensor is fixed to the upper jaw.

13. The device as set forth in claim 12, wherein said reference sensor is fixed to a tooth of the upper jaw.

14. The device as set forth in claim 11, wherein said reference sensor is removably fixed by means of an adaptor attached to the upper jaw or tooth.

* * * * *